(12) United States Patent
Reimann

(10) Patent No.: US 9,322,634 B2
(45) Date of Patent: Apr. 26, 2016

(54) SENSOR ARRANGEMENT AND METHOD FOR OPERATION OF AN OPERATING DEVICE

(71) Applicant: Siemens Aktiengesellschaft, Munich (DE)

(72) Inventor: Michael Reimann, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 31 days.

(21) Appl. No.: 14/312,986

(22) Filed: Jun. 24, 2014

(65) Prior Publication Data
US 2015/0008943 A1 Jan. 8, 2015

(30) Foreign Application Priority Data

Jul. 3, 2013 (EP) .................................... 13174912

(51) Int. Cl.
*G01R 27/26* (2006.01)
*G01B 7/004* (2006.01)
*H03K 17/94* (2006.01)
*H03K 17/96* (2006.01)
*G01N 21/94* (2006.01)

(52) U.S. Cl.
CPC ................ *G01B 7/004* (2013.01); *G01N 21/94* (2013.01); *H03K 17/941* (2013.01); *H03K 17/962* (2013.01); *H03K 17/9627* (2013.01); *H03K 2217/94106* (2013.01); *H03K 2217/960705* (2013.01); *H03K 2217/960755* (2013.01)

(58) Field of Classification Search
CPC .............. H03K 17/941; H03K 17/962; H03K 2217/94116; H03K 2217/960705
USPC .................................... 324/684, 679; 250/221
See application file for complete search history.

(56) References Cited

U.S. PATENT DOCUMENTS 5,410,148 A 4/1995 Barron, Jr.

FOREIGN PATENT DOCUMENTS

DE 10 2007 008 007 A1 8/2008
EP 2 479 894 A1 7/2012

*Primary Examiner* — Vincent Q Nguyen
(74) *Attorney, Agent, or Firm* — Cozen O'Connor

(57) ABSTRACT

A sensor arrangement comprises an input surface, an optical sensor, a first capacitive sensor, an evaluation unit and a device. The input surface has at least one light-permeable part surface. The optical sensor is disposed below the at least one light-permeable part surface. The first capacitive sensor is disposed below the input surface. The evaluation unit is coupled to the optical sensor and configured to carry out a light-permeability measurement of an object located on the input surface using the optical sensor. The device is configured to evaluate a change in capacitance of the first capacitive sensor. The device is connected to the first capacitive sensor and further configured to generate a first output signal if there is a change in capacitance. The evaluation unit is further configured to generate a presence signal if a measured light permeability falls below a predetermined value.

9 Claims, 1 Drawing Sheet

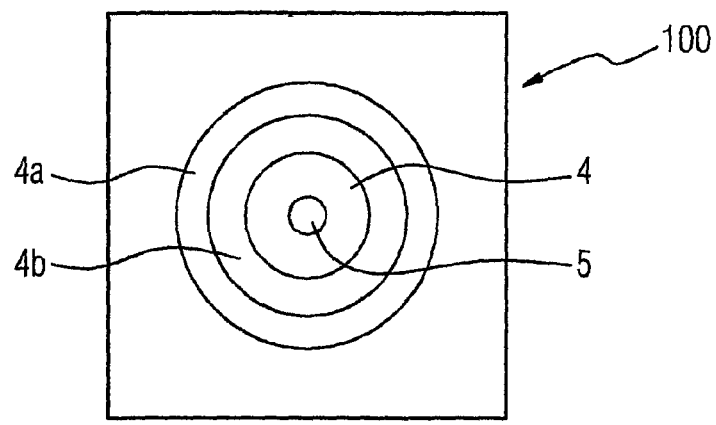
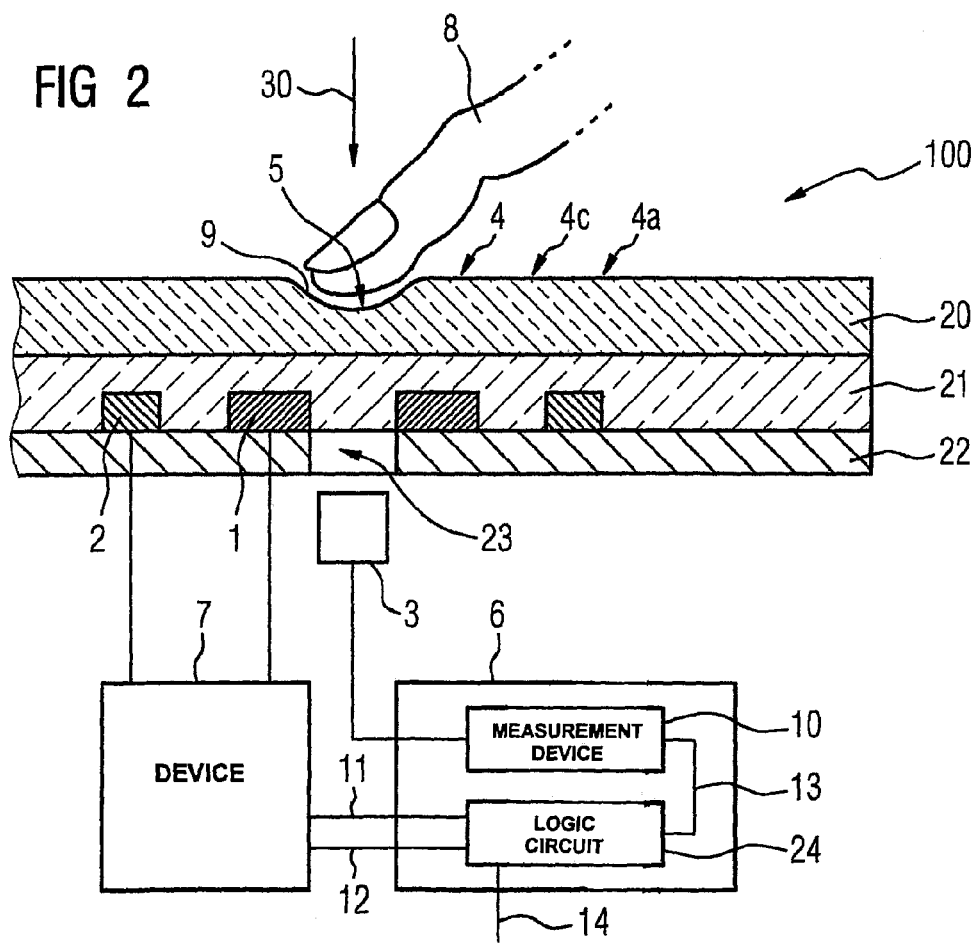

SENSOR ARRANGEMENT AND METHOD FOR OPERATION OF AN OPERATING DEVICE

FIELD OF INVENTION

The invention relates to a sensor arrangement comprising an input surface below which a first capacitive sensor is disposed and a device for evaluating a change in capacitance of the first sensor. The device is connected to the first sensor, and configured to provide a first output signal if there is a change in capacitance. Furthermore the invention relates to a method for operation of an operating device with at least one sensor arrangement, wherein an input surface is assigned to a first capacitive sensor. A touch on the input surface is evaluated capacitively and a first output signal is provided for an operator control action, wherein a change in capacitance of the first capacitive sensor is received as an operator control action.

DESCRIPTION OF THE RELATED ART

Capacitive sensor arrangements are used as operating elements for electrical devices, such as hob plates, automatic coffee makers, medical devices and human machine interface (HMI) devices for industrial automation. An individual capacitive sensor with an evaluation unit converts a manual actuation into an electrical switching signal in that the electrical field transmitted by the sensor is changed by the intrusion of an electrically-conducting object, such as a human finger. These changes of the electric field are detected by the evaluation device so that a switching signal is generated by the evaluation device for a corresponding change in capacitance. Such sensors or sensor arrangements are employed as, e.g., buttons and make it possible, e.g., to switch on or switch off electrical devices. In such cases, the capacitive sensors are connected electrically to a printed circuit board or to the evaluation device and are supplied with power by the evaluation device. The capacitive sensors are permanently monitored for a change in capacitance.

Cover plates (e.g., ones that are especially made of glass or another transparent non-conductive substance) often serve as an outer delimitation for the sensor and thus form an input surface, which can be touched by a human finger or an electrically-conductive object. The capacitance field generated by a capacitive sensor has a spatial extent and passes through the electrically non-conductive cover plate without being deflected by the latter, so that the spatial capacitance field is present on the outer side of the cover plate in the area of the input surface. As soon as an operating object, such as a human finger, intrudes into the capacitance field, this capacitance field change is detected by the sensor and is passed on to the evaluation device so that the electrical switching signal is created by this sensor.

With such capacitive buttons, however, unintentional switching processes can arise if, for example, a film of moisture gets into the area of the input surface. A capacitance field change is likewise achieved by the film of moisture which is detected by the evaluation device. The evaluation device may not be able to distinguish whether the capacitance field variation has been caused by an intentional and correct touch by a control object, such as a human finger, or by a film of moisture. In European patent application EP 2 479 894 A1, a capacitive button for creating an electrically-evaluable switching signal is disclosed.

SUMMARY OF THE INVENTION

An object of the present invention is to improve the capacitive button of EP 2 479 894 A1 by addressing the disadvantage associated with incorrect inputs that are caused by, e.g., films of moisture.

The object is achieved, for the sensor arrangement described above, by the input surface having at least one light-permeable part surface and by an optical sensor being arranged below the part surface, wherein the optical sensor is attached to an evaluation unit and the evaluation unit is equipped to carry out a light-permeability measurement, using the optical sensor, of an object located on the input surface and to generate a presence signal if a light permeability determined is below a predetermined value. If the light permeability falls below the predetermined value, the evaluation unit is configured to evaluate the first output signal and the presence signal and, if both signals are present, to provide a validity signal. Using the light permeability measurement (i.e., an optical measurement) method, it is determined whether a control object, such as a human finger, or film of moisture, water, cleaning fluid or mushy substances, as can for example arise in the production of foodstuffs, is located on the surface of the sensor. This utilizes the fact that a human finger darkens the optical sensor far more than water or the mushy substances.

In order to further improve the sensor arrangement with respect to incorrect inputs, the sensor arrangement includes a supplementary surface, below which a second capacitive sensor is disposed. The supplementary surface at least partially surrounds the input surface. The device for evaluating a change in capacitance of the first sensor is further configured to evaluate a change in capacitance of the second sensor and to generate an output signal if the capacitance has changed. The evaluation unit is further configured to evaluate the second output signal and, if the second output signal is present, to withdraw the validity signal again. If there is film of moisture on the sensor arrangement, for example, then the second capacitive sensor of the supplementary surface is also influenced by the film of moisture. If, for example, the finger of a human hand is now located exactly in the center of the input surface, wherein this presence of the human finger on the input surface has been registered by the optical sensor, but film of moisture is additionally present which could cause an incorrect measurement, then the validity signal, which was created as a result of the optical sensor, is withdrawn again.

In one embodiment, the sensor arrangement has a depression for a control object (e.g., a human finger) within the input surface, wherein the optical sensor is disposed below the finger depression. A finger depression additionally enables light shining in from the side to be minimized or suppressed entirely and thus a safe result for the presence of an operating object can be created.

Advantageously the supplementary surface is disposed around the input surface in the form of a ring. In this case it is also advantageous for a corridor, or an area, to be disposed between the input surface and the supplementary surface, which is essentially free from an electric flux of the capacitive sensors. This means that the first sensor and the second sensor are disposed at a distance from one another and if the first sensor is not touched exactly in the center, by a human finger for example, this does not result in the validity signal being suppressed.

The object described at the start is also achieved by a method for operation of an operating device with at least one sensor arrangement. An input surface is assigned to a first capacitive sensor, wherein a touch on the input surface is evaluated capacitively and a first output signal is generated for an operator control action. For instance, a change in capacitance of the first capacitive sensor is received as an operator control action. In order to avoid incorrect inputs in the operating device with capacitive sensors, a measurement of an object located on the input surface is performed using an optical sensor, and a check is made as to whether a light permeability determined is below a predetermined value. If the value is below the predetermined value, a presence signal is generated. A check is also made as to whether the first output signal and the presence signal are present, and if both signals are present a validity signal is provided, through which the operator control action is recognized as valid. Through the light-permeability measurement or the optical measurement method resulting therefrom, it is to be determined whether, for example, a human finger or film of moisture is located on the sensor arrangement. This utilizes the fact that, for example, the human finger darkens the sensor much more than the film of moisture.

The method is further optimized if a supplementary surface is assigned to a second capacitive sensor and a touch on the supplementary surface is evaluated capacitively and a second output signal is generated for a touch on the supplementary surface. For example, a change in capacitance of the second capacitive sensor is received as an incorrect operation and, if the second output signal is present, the validity signal is withdrawn. If the sensor arrangement is disposed, for example, in an HMI operating device of industrial automation, and if this HMI operating device is cleaned with a jet of water, for example, this jet of water will trigger both sensors, which would result in incorrect operation, but an evaluation unit, such as a microcontroller, is adapted to logically combine the measurement results of the two capacitive sensors and accordingly to declare an operator control action invalid.

Preferably, an electric flux of the second sensor is essentially aligned in a ring shape around the input surface.

Furthermore, it is of advantage for the electric flux of the second sensor and an electric flux of the first sensor to be aligned such that a corridor arises between the input surface and the supplementary surface, which is essentially free from an electric flux of the capacitive sensors.

BRIEF DESCRIPTION OF THE DRAWINGS

The drawing shows an exemplary embodiment of the invention. In the drawing:

FIG. 1 shows a sensor arrangement viewed from above in accordance with one embodiment of the present invention; and FIG. 2 shows the sensor arrangement in a schematic sectional diagram in accordance with one embodiment of the present invention.

DETAILED DESCRIPTION OF THE PRESENTLY PREFERRED EMBODIMENTS

A sensor arrangement 100, comprising an input surface 4, below which a first capacitive sensor 1 (see FIG. 2) is disposed, is shown in FIG. 1. Disposed around the input surface 4 in the form of a ring is a supplementary surface 4a. Disposed in the input surface 4 is a light-permeable part surface 5, below which an optical sensor 3 (see FIG. 2) is disposed. If the sensor arrangement 100 is disposed for example in an operating device and if film of water were to flow over the operating device or over the sensor arrangement 100, the film of water would touch the input surface 4 and cause a change in capacitance, through which an unwanted switching signal would be generated. To prevent this, the part surface 5 is disposed in the input surface 4. Since the part surface 5 is light-permeable and an optical sensor 3 is disposed below it, an operator control action on the sensor arrangement 100 is only declared valid if, using the optical sensor 3, a light-permeability measurement of an object 8 located on the input surface 4 (see FIG. 2) has resulted in a light permeability having a value below a predetermined value. A finger of a human hand for example will thus darken the part surface 4, so that this criterion is fulfilled. Film of water, on the other hand, will not darken the part surface 5 in this way.

FIG. 2 depicts the sensor arrangement 100 shown in FIG. 1 in a sectional diagram. The first capacitive sensor 1 and the second capacitive sensor 2 are disposed within a transparent connection layer 21. A protective layer 20, made of glass for example, serves as an operating surface. The protective layer 20 and the transparent connecting layer 21, in turn, are disposed on a carrier plate 22. The first capacitive sensor 1 and the second capacitive sensor 2 are each connected to a device 7 for evaluating a change in capacitance of the sensors 1, 2.

The input surface 4 and the supplementary surface 4a are disposed in the protective layer 20 in a ring shape, and a corridor 4b is disposed between the input surface 4 and the supplementary surface 4a. Disposed in the center of the first capacitive sensor 1 is a depression 23 which is permeable to light. Incident light 30 on the protective layer 20 can thus reach an optical sensor 3 through the depression 23. The optical sensor 3 in turn is connected to the evaluation unit 6. The evaluation unit 6 in this case is coupled to the optical sensor 3 to perform a light-permeability measurement of an object 8 located on the input surface 4, such as a finger of a human hand, and to create a presence signal 13 if a determined light permeability is below a predetermined value. The light-permeability measurement is carried out with a measurement device 10.

If there is a change in capacitance of the first sensor 1, the change in capacitance of the first sensor 1 is detected by the device 7 using an output signal 11. A change in capacitance of the second sensor 2 is indicated using the output signal of the device 7 as a second output signal 12.

The evaluation unit 6 may be further configured to evaluate the first output signal 11 and the presence signal 13 and, if both signals are present, to provide a validity signal 14.

To further increase the input security, the evaluation unit 6 is also configured to evaluate the second output signal 12 and, if the second output signal 12 is present, to withdraw the validity signal 14 again. These evaluations of the output signals 11, 12 and of the presence signal 13 are preferably carried out in a logic circuit 24, which provides the validity signal 14 as its output.

Preferably, a red-green-blue (RGB) colored light sensor, especially a silicon chip-based light sensor, such as a photodiode, is used as the optical sensor 3.

The above-described sensor arrangement improves the ability to recognize incorrect operations in the environments which need frequent cleaning as well as the environments which are subjected to contamination of a display of an operating device by partly-transparent, conductive substances. A basic brightness of the environment would have to be defined in such cases and is dependent on the sensitivity of the optical measurement method used.

The series of detailed descriptions set forth above are only specific descriptions directed to the feasible embodiments of the present invention, and are not intended to limit the scope of protection of the present invention; and all the equivalent embodiments or modifications made without departing from the technical spirit of the present invention shall be included in the scope of protection of the present invention.

What is claimed is:

1. A sensor arrangement, comprising:
   an input surface having at least one light-permeable part surface;
   an optical sensor that is disposed below the at least one light-permeable part surface;
   a first capacitive sensor that is disposed below the input surface;
   an evaluation unit coupled to the optical sensor and configured to carry out a light-permeability measurement of an object located on the input surface using the optical sensor; and
   a device for evaluating a change in capacitance of the first capacitive sensor, wherein the device is connected to the first capacitive sensor and configured to generate a first output signal if there is a change in capacitance,
   wherein the evaluation unit is further configured to generate a presence signal if a measured light permeability determined falls below a predetermined value, and
   wherein, if the light permeability is determined to fall below the predetermined value, the evaluation unit is further configured to evaluate the first output signal and the presence signal and, if both signals are present, to generate a validity signal.

2. The sensor arrangement of claim 1, further comprising a second capacitive sensor, wherein the input surface also has a supplementary surface which at least partially surrounds the input surface, wherein the second capacitive sensor is disposed below the supplementary surface, wherein the device is further configured to evaluate a change in capacitance of the second sensor and, if the capacitance has changed, to provide a second output signal, and wherein the evaluation unit is further configured to evaluate the second output signal and, if the second output signal is present, to withdraw the validity signal.

3. The sensor arrangement of claim 2, wherein the supplementary surface is disposed around the input surface in the shape of a ring.

4. The sensor arrangement of claim 2, wherein a corridor, which is essentially free from an electric flux of the capacitive sensors, is disposed between the input surface and the supplementary surface.

5. The sensor arrangement of claim 1, wherein a depression for the object is disposed within the input surface and the optical sensor is disposed below the object depression.

6. A method for operating an operating device with at least one sensor arrangement of claim 1, wherein an input surface is assigned to a first capacitive sensor, wherein a touch on the input surface is evaluated capacitively and a first output signal is generated for an operator control action, wherein a change in capacitance of the first capacitive sensor is received as an operator control action, wherein a light-permeability measurement of an object located on the input surface is performed using an optical sensor and a check is made to determine whether a light permeability falls below a predetermined value, wherein, if the value is below the predetermined value, a presence signal is created and a check is made to determine whether both the first output signal and the presence signal are present, and if the two signals are present, a validity signal is generated, and wherein the operator control action is recognized as valid if the two signals are present.

7. The method of claim 6, wherein a supplementary surface is assigned to the second capacitive sensor and a touch on the supplementary surface is evaluated capacitively, wherein a second output signal for a touch on the supplementary surface is generate, and wherein a change in capacitance of the second capacitive sensor is received as an incorrect operation, and if the second output signal is present, the validity signal is withdrawn.

8. The method of claim 7, wherein an electric flux of the second sensor is essentially aligned in a ring shape around the input surface.

9. The method of claim 7, whereby the electric flux of the second sensor and an electric flux of the first sensor are aligned so that a corridor, which is essentially free from an electric flux of the capacitive sensors, arises between the input surface and the supplementary surface.

* * * * *